US005662923A

United States Patent [19]
Roreger

[11] Patent Number: 5,662,923
[45] Date of Patent: Sep. 2, 1997

[54] PLASTER FOR THE TRANSDERMAL APPLICATION OF STEROID HORMONES, CONTAINING DEXPANTHENOL

[75] Inventor: Michael Roreger, Neuwied, Germany

[73] Assignee: LTS Lohmann Therapie-Systeme GmbH & Co., Neuwied, Germany

[21] Appl. No.: 397,168

[22] PCT Filed: Aug. 16, 1993

[86] PCT No.: PCT/EP93/02182

§ 371 Date: May 16, 1995

§ 102(e) Date: May 16, 1995

[87] PCT Pub. No.: WO94/06436

PCT Pub. Date: Mar. 31, 1994

[30] Foreign Application Priority Data

Sep. 12, 1992 [DE] Germany ............ 42 30 588.8

[51] Int. Cl.$^6$ ............................................. A61L 15/00
[52] U.S. Cl. ..................... 424/445; 424/448; 424/449
[58] Field of Search ........................... 424/448, 449, 424/445

[56] References Cited

U.S. PATENT DOCUMENTS 4,994,267  2/1991  Sablotsky ............ 424/78

FOREIGN PATENT DOCUMENTS 0 285 563  10/1988  European Pat. Off. .

OTHER PUBLICATIONS

The Merck Index, 9th ed., Martha Windholz Editor p. 386, 1976.

Primary Examiner—D. Gabrielle Phelan
Attorney, Agent, or Firm—Wenderoth, Lind & Ponack

[57] ABSTRACT

Self-adhesive plaster for the transdermal application of systemically active steroid hormones, comprising an active substance-impermeable backing layer, an active substance-containing pressure-sensitive adhesive layer and a detachable protective layer which, prior to application to the skin, covers said pressure-sensitive adhesive layer, characterized in that the active substance-containing pressure-sensitive adhesive layer comprises a pressure-sensitive hot melt adhesive having a processing temperature of between 60° an 100° C., and dexpanthenol in a concentration of 15 to 25%-wt.

10 Claims, No Drawings

PLASTER FOR THE TRANSDERMAL APPLICATION OF STEROID HORMONES, CONTAINING DEXPANTHENOL

This application is a 371 of PCT/EP93/02182, filed Aug. 16, 1993.

DESCRIPTION

The invention relates to a self-adhesive plaster for the transdermal application of systemically active steroid hormones, comprising an active substance-impermeable backing layer, an active substance-containing pressure-sensitive adhesive layer and a removable protective layer covering said pressure-sensitive adhesive layer prior to application to the skin.

Active substance plasters as therapeutic systems (TTS) are self-adhesive devices to be applied to the skin, having a defined application surface and releasing one or more drugs contained therein to the human or animal body in a controlled manner as to time and amount.

However, it is a prerequisite for transdermal active substance absorption, that the active substance in the galenic formulation be provided in a form permitting its absorption by the skin, which means that the active substance must be at least partially dissolved in the formulation. The steroid hormones, and in particular the active substance estradiol, which among the substances of this group is the one most thoroughly tested for transdermal administration, are known to exhibit only a very low solubility in those formulations which are commonly suitable for transdermal active substance release and are commonly used for this purpose. In such formulations, wherein as base polymers for example polyacrylates or polyisobutylenes are utilized, generally recrystallisation of the active substance occurs during storage of the plaster, which alters the release behaviour and thus the resorption behaviour.

In principle, there is a possibility to maintain the solubility of the active substance during storage and to prevent recrystallization by employing solubilizers.

In estradiol TTS which have been available on the market under the trademark "Estraderm", estradiol and ethanol are administered as solvents for estradiol in a plaster formulation containing the active substance solution in a bag (EP 0 285 563). Disadvantages of this plaster are first its complicated structure and complicated, costly manufacture, and secondly the fact that, in particular in the case of application over a period of several days, skin irritations may occur caused by the solubilizer ethanol.

In transdermal therapeutic systems of common construction-comprising single-layered, self-adhesive active substance matrices, for example—the use of solubilizers at a concentration which is at least equal to that required results in loss of cohesion, i.e. in the matrices becoming "mushy". This especially applies to dexpanthenol, a liquid which is highly viscous at room temperature and which in common formulations has a highly softening effect, even at comparatively low concentrations. EP 0 380 989 describes dexpanthenol as a penetration auxiliary substance in the transdermal administration of systemically effective, pharmaceutic active substances. It is stated to be a particular advantage of the use of dexpanthenol that dexpanthenol does not only have a penetration enhancing effect but also suppresses or reduces the skin irritating influence of active substances and auxiliary substances.

In addition, tests carried out by the applicant of the present application have shown that dexpanthenol is a good solvent and a good solubilizer for steroid hormones.

It was thus the object of the present invention to provide an application of steroid hormones for a plaster for transdermal formulation permitting incorporation into the formulations of dexpanthenol at concentrations not below those required for solubilization while avoiding both loss of cohesion and deliquescence of the active substance-containing plaster component during application.

Surprisingly, this object was achieved in that the active substance-containing pressure-sensitive layer contains a pressure-sensitive hot melt adhesive with a processing temperature of 60° to 100° C., and a portion of dexpanthenol of from 15 to 25%-wt.

Since, commonly, formulations for the transdermal application of systemically active steroid hormones contain the respective steroid hormone, e.g. estradiol, at a concentration of 1 to 2%, and considering the respective saturation solubility of the steroid hormone in dexpanthenol, a portion of at least 15%-wt. of dexpanthenol is required in order to reliably prevent crystallization of the active substance in the formulation. Despite expectations to the contrary, it is possible to achieve such a concentration of dexpanthenol in an active-substance-containing formulation for transdermal application while avoiding the loss of inner cohesion of the pressure-sensitive adhesive formulation, if a pressure-sensitive hot melt adhesive having a processing temperature of 60° to 100° C. is selected.

Pressure-sensitive hot melt adhesives are solid, thermoplastic formulations, substantially containing substances of the group consisting of polymers, resins, fillers and ageing protecting agents.

For this purpose, homopolymers, copolymers or block polymers, such as polyamides, polyesters, polycaprolactames, polycaprolactones, ethylene-vinylacetate copolymers (EVA), ethylene-ethylacrylate copolymers (EEA), polyvinyl ethers, poly(meth)acrylates, polyvinyl acetales, polyvinyl acetates, styrene-butadiene block polymers, isoprene block polymers, polyurethanes, ethylcellulose, cellulose acetate butyrate, synthetic rubbers (e.g. neoprene rubber), polyisobutylene, butyl rubber, acrylonitrile butadiene copolymers, epoxide resins, melamine resins, phenol-formaldehyde resins and resorcinol formaldehyde resins may be used as polymers, it being also possible to use, inter alia, the following modified resins: hydrogenated colophony, polymerized colophony, dimerized resin acids, disproportionated colophony, methyl esters of colophony, glycerin esters of hydrogenated colophony, methyl esters of hydrogenated colophony, pental esters, triethylene glycol esters of hydrogenated colophony, hydroabietyl alcohol and its derivatives, glycerin esters, di-triol esters and pental esters of resin acids, pental esters of polymerized colophony, pental esters of dimerized colophony, glycerin esters of dimerized colophony, esters of maleic acid-modified or phenol-modified colophony, aromatic and aliphatic hydrocarbon resins, hydrogenated resins, polyterpene resins, modified terpene resins, waxes, low-molecular polyethylene and polypropylene, alkyl-styrene copolymers. In addition, fillers may be admixed, such as titanium dioxide, magnesium dioxide, zinc oxide and silicon dioxide, as well as ageing protecting agents, such as tocopherol substituted phenols, hydroquinones, pyrocatechines and aromatic amines.

Pressure-sensitive hot melt adhesives of the kind mentioned above are processed at temperatures of between 60° and 100° C. in melted condition and solidify while forming adhesive and cohesive forces; the cohesive forces generally decrease with decreasing softening temperatures of the pressure-sensitive hot melt adhesives.

The softening temperature is in particular reduced by so-called plasticizers, which also include dexpanthenol, whereby, generally, low concentrations of plasticizers already result in a marked loss of cohesion. As already mentioned above, the plasticizer dexpanthenol, surprisingly, can be incorporated into pressure-sensitive hot melt formulations in unusually high concentrations, whereby the above-mentioned loss of cohesion has not been observed. However, the plasticizer absorption capacity of a pressure-sensitive hot melt formulation according to the present invention having a processing temperature of between 60° and 100° C. is limited as well.

Where the dexpanthenol portion is above 25%-wt., in the beforementioned pressure-sensitive hot melt adhesives too a reduction of the melt temperature occurs within a range near the body temperature so that, upon application of such formulations to the skin, unwanted softening occurs.

When formulating active substance-containing pressure-sensitive hot melt adhesives for the transdermal application of systemically active steroid hormones, the temperatures required for the manufacture and processing of the pressure-sensitive hot melt adhesive must be kept within a range which precludes unwanted changes in the steroid hormone or in other formulation components. The temperature stability of the known steroid hormones is quite good at temperatures of below 100° C., so that a pressure-sensitive hot melt formulation for steroid hormones ideally exhibits a processing temperature of below 100° C. On the other hand, the processing temperature should be above 60° C. in order to attain a sufficient cohesion of the pressure-sensitive hot melt adhesive after cooling down.

A pressure-sensitive hot melt adhesive that is particularly suited to meet the requirements with regard to processing temperature (60° to 100° C.), cohesion of the formulation (max. 25%-wt. dexpanthenol) and solubility of the steroid hormone (at least 15% dexpanthenol) is a dexpanthenol-containing pressure-sensitive hot melt adhesive having the following composition:

10 to 30%-wt. of ethylene-vinylacetate copolymer having a vinyl acetate content of 28%

15 to 45%-wt. flexible resin having a melt viscosity of below 10 Pa.s at 60° C.

10 to 30%-wt. aliphatic hydrocarbon resin having a melt viscosity above 10 Pa.s at 100° C.

15 to 25%-wt. dexpanthenol 0.1 to 10%-wt. steroid hormone 0 to 5%-wt. filler 0 to 5%-wt. ageing protecting agent.

A pressure-sensitive hot melt adhesive formulation of the above-mentioned composition may also contain 16.7%-wt. ethylene-vinylacetate copolymer having a vinylacetate content of 28%

35.8%-wt. hydroabietyl alcohol 23.2%-wt. polyalkadiene (chain length of the monomer $C_4$ to $C_5$)

21.6%-wt. dexpanthenol 0.7%-wt. silicon dioxide 2.0%-wt. estradiol

If this formulation, after melting and homogenizing at a temperature of, for example, 90° C., is spread onto a carrier material, a homogeneous, transparent film is obtained, wherein even 12 months after preparation no estradiol crystals will be found in microscopic examinations.

If a pressure-sensitive hot melt adhesive formulation of the same composition, however, without the addition of dexpanthenol, is prepared, the active substance estradiol, which is to be incorporated, cannot be completely dissolved. After spreading and cooling of the pressure-sensitive hot melt adhesive, crystallization of the active substance from the oversaturated solution quickly occurs, as well as continuing crystalline growth, especially in those places where crystals are already present which have not dissolved in the melt.

The above-described example, on the one hand, illustrates the fact that dexpanthenol is particularly suited for solubilization in those cases where steroid hormones are to be dissolved in pressure-sensitive hot melt adhesives having a processing temperature of 60° to 100° C.; on the other hand, the example shows the ability of dexpanthenol to stabilize the state of the oversaturated solution of steroid hormones in the pressure-sensitive hot melt adhesive and to prevent recrystallization of the steroid hormone and thus the destabilization of the system.

Systemically active steroid hormones according to the present invention may be estrogens, for example. These include the most effective one of the natural estrogens, 17-β-estradiol, as well as esters, ethers or ethinyl compounds of estradiol, such as estradiol (17β)-17-butyryl acetate, estradiol 17-β-cipionate, estradiol 13,17-β-dienantate, estradiol 3,17-β-dipropionate, estradiol enantate, estradiol 3-hydrogen sulfate (sodium salt), estradiol 17-β-(3-phenylpropionate), estradiol undecylate, estradiol valerate, estradiol 17-(oxohexonate), epimestrol, quinestrol, quinestradol, ethinyl estradiol, fosferol, as well as estratriol.

In addition, systemically active steroid hormones according to the invention may be progestagens, such as:

lynestrenol, norethisterone, hydroxyprogesterone, progesterone, medroxyprogesterone, gestonorone, dydrogesterone, chloromadinone, allylestrenol, megestrol, medrogestone.

Dexpanthenol-containing plasters for the transdermal application of systemically active steroid hormones wherein the active substance-releasing part contains pressure-sensitive hot melt adhesives may be construed according to any plaster construction known to those skilled in the art, for example according to the matrix system or the membrane system.

A membrane system comprises at least 5 members: a flexible backing layer, an active substance-containing pressure-sensitive hot melt adhesive, a membrane for controlling the active substance release, an adhesive layer laminated on the membrane for fixing the system to the skin, as well as a removable protective layer covering the skin-facing, adhesive surface of the plaster.

A matrix system in its most simple form comprises three members: a flexible backing layer, an active substance-containing pressure-sensitive hot melt adhesive and a removable protective layer covering the skin-facing, adhesive surface of the plaster.

Suitable backing layer materials are, for example, ester, polyamide, polyethylene, polypropylene, polyurethane, polyvinylchloride, both as single-layered films and as sandwich films in combinations of films of different ones of these plastics. These films may also be aluminized or laminated with an aluminium foil.

Suitable materials for the removable protective layer are, for example, polyester, polyethylene and polypropylene, as well as paper materials coated with these materials and optionally aluminized or laminated with an aluminium foil. In addition, the films or paper materials are coated with silicone in order to render them detachable.

The active substance-releasing pressure-sensitive hot melt adhesive may be present in one or several layers. In the latter case, the composition of the layers may vary. In the individual layers, different auxiliaries or different active substance concentrations are used in order to ensure that the active substance is released in such a manner as is required for application, and as cannot be achieved, for example, by using single-layered structures.

The present invention provides a process for the manufacture of a plaster according to the features as described hereinbelow:

a) resin portions of the formulation are melted at approx. 60° to 200° C., b) polymers are slowly stirred into the melt until a clear melt is obtained, c) subsequently or simultaneously, auxiliaries and/or fillers are slowly stirred into the mass until a homogeneous distribution is obtained (melt A), d) in a separate stirring vessel dexpanthenol is melted at 50° C.; estradiol is slowly stirred into the melt in portions until a clear solution is obtained (melt B)

e) melt B is slowly stirred into melt A until a homogeneous mixture is obtained, f) using a knife coating technique, the pressure-sensitive hot melt adhesive is thereafter spread at 60° to 100° C. onto a siliconized polyester protective layer (thickness 30 to 250 µm) such that a weight per area of 80 to 500 g/m$^2$, preferably 150 to 260 g/m$^2$, results; after cooling down, a backing layer of polyester (thickness 6 to 100 µm) is laminated onto the pressure-sensitive hot melt adhesive, g) subsequently, plasters having a thickness of 10 cm$^2$ are punched out.

The processing of the active substance-releasing pressure-sensitive adhesive layer containing pressure-sensitive hot melt adhesives with a processing temperature of between 60° and 100° C., may be carried out employing known procedures such as extrusion, casting, roll coating, knife coating, spray coating, or a printing process.

| Formulation Examples | 1 | 2 |
|---|---|---|
| Ethylene-vinylacetate copolymer comprising 28% vinyl acetate | 17.7 g | 16.7 g |
| Dexpanthenol | 15.9 g | 21.6 g |
| Hydroabietyl alcohol | 38.9 g | 35.8 g |
| Polyalkadiene (monomer chain length $C_4$ to $C_5$) | 24.7 g | 23.2 g |
| Silicon dioxide | 0.7 g | 0.7 g |
| Ethylcellulose | 0.7 g | |
| Estradiol | 1.4 g | 2.0 g |
| | 100.0 g | 100.0 g |
| Weight per area of the active substance-free pressure-sensitive adhesive layer (g/m$^2$) | 230 | 231 |
| Active substance content of the plaster (mg/10 cm$^2$) | 2.80 | 4.24 |
| Penetration of mouse skin (µg/10 cm$^2$) | | |
| 8 h | 33 | 38 |
| 24 h | 91 | 113 |
| 48 h | 257 | 340 |
| In vitro release (paddle over disc; µg/10 cm$^2$) | | |
| 4 h | 116 | 194 |
| 24 h | 430 | 752 |

The manufacture of the plasters according to the formulation examples 1 and 2 is carried out such that, for example, hydroabietyl alcohol is melted at 90° C. Ethylenevinylacetate copolymer and polyalkadiene are slowly stirred into the melt until it becomes clear. Thereafter, silicon dioxide and, in example 1, ethylcellulose are slowly stirred into the mass, until a homogeneous distribution is obtained (melt A).

Dexpanthenol is melted at 50° C. in a separate stirring vessel. Estradiol is slowly, and in portions, stirred into the melt until a clear solution is obtained (melt B).

Melt B is slowly stirred into melt A until a homogeneous distribution is obtained.

Using a knife coating process, the pressure-sensitive hot melt adhesive is spread onto a siliconized polyester protective layer (thickness 100 µm) such that a weight per area of 230 g/m$^2$ is obtained. After cooling down, a polyester backing layer (thickness 15 µm) is laminated onto the pressure-sensitive hot melt adhesive.

Subsequently plasters having an area of 10 cm$^2$ are punched out.

Examinations of these plasters with regard to penetration through excised mouse skin and in-vitro release have shown that the plaster according to the invention ensures optimum penetration values while preventing the occurrence of crystallization.

I claim:

1. In a self-adhesive plaster for the transdermal application of a systemically active steroid hormone which plaster comprises (1) an active substance-impermeable flexible backing layer (2) an active substance reservoir connected to said layer and comprising a pressure-sensitive hot melt adhesive, and (3) a protective layer covering the skin-facing adhesive surface of the plaster and being detachable prior to application of the plaster to the skin, the improvement wherein the pressure-sensitive adhesive is a pressure-sensitive hot melt adhesive from which an active substance-containing layer is formed by processing at a temperature of between 60° and 100° C. in molten condition, which leads to the formation of adhesive and cohesive forces in the process, and wherein the pressure-sensitive hot melt adhesive contains the following components:

(a) 10 to 30%-wt. ethylene-vinylacetate copolymer,
(b) 15 to 45%-wt. flexible resin having a melt-viscosity of below 10 Pa.s at 60° C.,
(c) 10 to 30%-wt. aliphatic hydrocarbon resin having a melt viscosity above 10 Pa.s at 100° C.,
(d) 15 to 25%-wt. dexpanthenol as recrystallization inhibitor,
(e) 0.1 to 10%-wt. female sex steroid hormone,
(f) 0 to 5%-wt. filler, and
(g) 0 to 5%-wt. ageing protecting agent, the sum of the percentages of the components being 100.

2. A plaster according to claim 1, wherein the female sex steroid hormone is estradiol.

3. A plaster according to claim 1 or 2, wherein the pressure-sensitive hot melt adhesive contains at least one polymer and auxiliary substances.

4. A plaster according to claim 3 wherein the pressure-sensitive hot melt adhesive contains as auxiliary substances at least one member of the group consisting of flexible resins, hardened resins, fillers and ageing protesting agents.

5. A plaster according to claim 1 or 2, wherein the pressure-sensitive hot melt adhesive contains ethylene-vinylacetate copolymer having a vinyl acetate content of 20 to 35%.

6. A plaster according to claim 1 or 2, wherein the active substance reservoir comprises a plurality of layers at least one of which contains the said pressure-sensitive hot melt adhesive.

7. A plaster according to claim 1 or 2, wherein the structure contains a membrane covering the active substance reservoir and which controls the release of the active substance, said membrane being connected to a pressure-sensitive adhesive member for fixation to the skin.

8. A process for the production of a plaster as defined in claim 1 comprising the following process steps:

a) resin portions of the formulation are melted at a temperature of about 60° to 200° C.,
b) polymers are slowly stirred into the melt until a clear melt is obtained,
c) subsequently or simultaneously, auxiliary substances and/or fillers are slowly added while stirring, until a homogeneous distribution is obtained (melt A),
d) in a separate stirring vessel dexpanthenol is melted at 50° C. and female sex steroid hormone is slowly added in portions while stirring, until a clear solution is obtained (melt B),
e) melt B is slowly stirred into melt A, until a homogeneous mixture is obtained,
f) using a knife coating technique, the pressure-sensitive hot melt adhesive is thereafter spread at a temperature of 60° to 100° C. onto a siliconised polyester protective layer having a thickness of 30 to 250 μm such that a weight per area of 80 to 500 g/m$^2$ is obtained; after cooling down, a backing layer of polyester having a thickness of 6 to 100 μm is laminated onto a pressure-sensitive hot melt adhesive, and
g) subsequently, patches are punched out.

9. A process according to claim 8, wherein the weight per area of the pressure-sensitive hot melt adhesive is 150 to 280 g/m$^2$.

10. A process according to claim 8 wherein the female sex steroid hormone is estradiol.

* * * * *